US012805798B2

(12) United States Patent
Odderson

(10) Patent No.: US 12,805,798 B2
(45) Date of Patent: Nov. 24, 2026

(54) METHOD OF TREATING CERVICAL VERTIGO

(71) Applicant: Ib R. Odderson, Kirkland, WA (US)

(72) Inventor: Ib R. Odderson, Kirkland, WA (US)

( * ) Notice: Subject to any disclaimer, the term of this patent is extended or adjusted under 35 U.S.C. 154(b) by 297 days.

(21) Appl. No.: 18/526,717

(22) Filed: Dec. 1, 2023

(65) Prior Publication Data

US 2024/0108283 A1 Apr. 4, 2024

Related U.S. Application Data

(63) Continuation-in-part of application No. 17/157,787, filed on Jan. 25, 2021, now abandoned.

(60) Provisional application No. 62/964,923, filed on Jan. 23, 2020.

(51) Int. Cl.

| | |
|---|---|
| ***A61B 5/00*** | (2006.01) |
| ***A61B 5/296*** | (2021.01) |
| ***A61B 5/397*** | (2021.01) |
| ***A61K 38/48*** | (2006.01) |

(52) U.S. Cl.

CPC ............ *A61B 5/4836* (2013.01); *A61B 5/296* (2021.01); *A61B 5/397* (2021.01); *A61B 5/6822* (2013.01); *A61B 5/6848* (2013.01); *A61K 38/4893* (2013.01); *A61B 2560/06* (2013.01)

(58) Field of Classification Search

CPC ....... A61B 5/4836; A61B 5/296; A61B 5/397; A61B 5/6822; A61B 5/6848; A61B 2560/06; A61K 38/4893

See application file for complete search history.

(56) References Cited

PUBLICATIONS

Van Gerpen et al. (Muscle and Nerve vol. 23, pp. 1752-1756).*
Coban et al. (Erciyes Medical Journal vol. 40 No. 4, pp. 42-44).*

* cited by examiner

*Primary Examiner* — Robert A Zeman
(74) *Attorney, Agent, or Firm* — Dean A. Craine

(57) ABSTRACT

A method of quickly and effectively treating cervical vertigo by using EMG-guided injections of botulinum toxin into selective dystonic neck muscles. For each treatment, EMG-guided injections are used wherein an EMG needle is injected into the muscle. An EMG test is then performed using the EMG needle to determine if the muscle is overactive. If the muscle is overactive, a measured amount of botulinum toxin is administered into the muscle using the EMG needle. Muscles that are not overactive are not administered botulinum toxin. The above procedure is conducted in various neck muscles, such as the oblique capitis superior muscle, the oblique capitis inferior muscle, the longissimus capitis muscle, the trapezius, and the levator scapula.

5 Claims, 1 Drawing Sheet

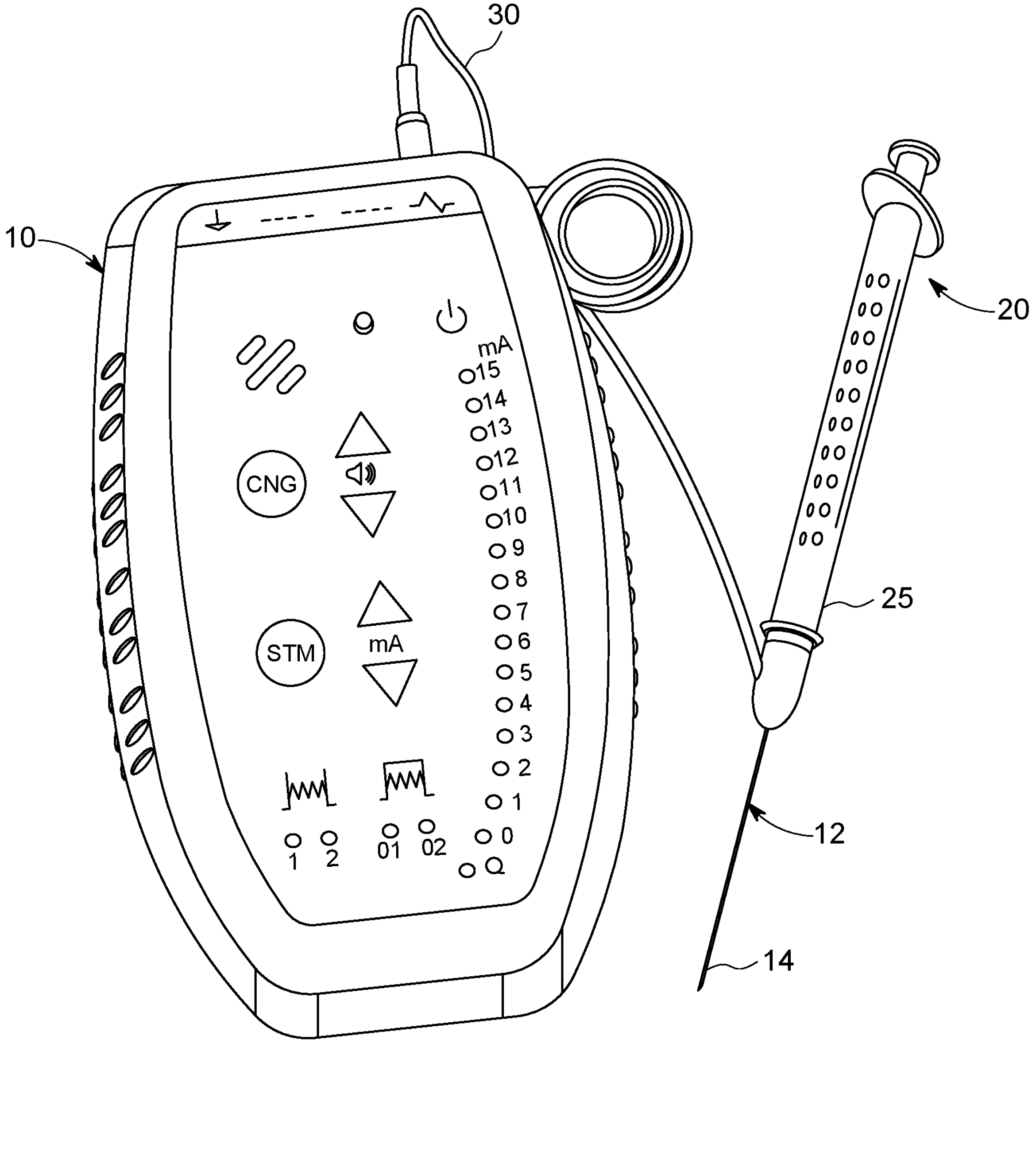
30
10
20
25
12
14
CNG
STM
mA
mA
15
14
13
12
11
10
9
8
7
6
5
4
3
2
1
0
1
2
01
02

METHOD OF TREATING CERVICAL VERTIGO

This is a continuation in part application based on the utility patent application (application Ser. No. 17/157,787), filed on Jan. 25, 2021 which was based on and claimed the filing date benefit of U.S. Provisional Patent Application (Application No. 62/964,923) filed on Jan. 23, 2020.

Notice is given that the following patent document contains original material subject to copyright protection. The copyright owner has no objection to the facsimile or digital download reproduction of all or part of the patent document, but otherwise reserves all copyrights.

BACKGROUND OF THE INVENTION

1. Field of the Invention

This invention pertains to method for treating cervical vertigo.

2. Description of the Related Art

Cervical Vertigo (CV) or Cervical Dizziness may occur after trauma to the head and neck such as whiplash injury, after overuse or have insidious onset. The underlying condition of cervical dystonia may not be readily recognized without specialized electrodiagnostic testing.

Heretofore, a patient who has had a neck injury and is experiencing vertigo, but not diagnosed with cervical dystonia, is typically treated with physical therapy, vestibular therapy, acupuncture, massage, chiropractic manipulations, trigger point injections, medications, radiofrequency ablation, greater occipital nerve block, and surgery. Unfortunately, all of these treatments are associated with variable success.

What is needed is a method for quickly and effectively treating cervical vertigo caused by dystonia of selected neck muscles.

SUMMARY OF THE INVENTION

A method of quickly and effectively treating cervical vertigo by using EMG-guided injections of botulinum toxin into selective dystonic neck muscles. The term 'EMG guided injections' refers to the combination of an EMG needle assembly that includes a hollow needle with an electrode at its tip attached to a hub that attaches to a Luer Lock or Slip Tip hub on a syringe body. The hub is attached to a lead wire that connects to an EMG machine. The needle shaft has an insulated coating with an exposed tip. The tip of the needle functions as an electrode. The hub is attached to a 3 to 10 ml syringe body with volume indica that holds a measurable amount of botulinum toxin.

When EMG-guided injections are used, the tip of the EMG needle is inserted into the muscle. The EMG is then activated, and an EMG test is then performed to determine if the muscle is overactive. The amount of overactivity is closely observed. If the muscle is overactive, the amount of botulinum toxin administered from the needle depends on the amount (0 to 25 units) of overactivity detected.

DESCRIPTION OF THE DRAWINGS

FIG. 1 is a top plan view of an EMG needle attached to a syringe filled with botulinum and attached to a portable EMG machine.

DESCRIPTION OF THE PREFERRED EMBODIMENT(S)

Disclosed herein is a method for treating cervical vertigo developed after a neck injury. The neck injury induced dystonia in selective neck muscles, which led to cervical vertigo. The method uses an EMG needle with a syringe body filled with botulinum toxin.

FIG. 1 shows a portable EMG device 10 attached to an EMG needle 12 and attached to a syringe body 20 containing botulinum toxin 25. The EMG needle 12 includes an electrode tip 14. A wire 30 extends from the hub to the EMG machine.

The portable EMG machine (also called an amplifier) and EMG needle are sold by Natus Medical Incorporated, located at 3150 Pleasant View Road, Middleton, WI 533362. The syringe body may be a 3 to 10 ml syringe body with standard hub.

During a treatment, the EMG needle is inserted into one or more neck muscles believed to be associated with cervical vertigo. Each muscle is individually tested for overactive. If a muscle is overactive, then a sufficient amount of botulinum toxin is injected into the muscle to reduce overactivity. The amount of botulinum toxin may be limited by the manufacturer of the botulinum toxin.

Case Presented:

A 54-year-old woman was hit by a wave in the back approximately ten years ago. She subsequently developed neck pain, vertigo spells, and muscle tension in the left trapezius. Vertigo sometimes occurred when she was lying in bed, with the first steps in the morning, and with full cervical rotation to the left. When the vertigo was severe, she felt nauseated and mostly had to lie down. She felt the dizziness was associated with tightness in the upper cervical muscles, including the oblique capitis superior and the inferior areas.

Testing for benign paroxysmal positional vertigo (BPPV) was negative, a course of prednisone and two cervical epidural steroid injections were given, all with short term benefits. A cervical MRI showed moderate to severe foraminal stenosis at R C3-4, and L C-6-7. Moderate foraminal stenosis at R C3-4, R C6-7, L C5-6 and L C7-T1. Mild foraminal stenosis at L C3-4.

An EMG assessment confirmed dystonia in the left trapezius, levator scapula, longissimus capitis, oblique capitis inferior, and oblique capitis superior.

A diagnosis of cervical dystonia was made based on her history, physical examination, head tilt to the left, limited cervical range of motion, and cervical dystonic muscular activity on EMG examination.

She was initially injected under EMG guidance with a total 100 units of incobotulinum toxin A (1:2 dilution in preservative-free saline) bilaterally to the oblique capitis superior muscles (OCS); (15 units+15 units) to the longissimus capitis muscle proximally; (15 units+15 units) and the trapezius (15 units) and the levator scapula distally (25 u).

The EMG needle was used to conduct an EMG test in the muscle and is also used to inject botulinum toxin into the muscle. The EMG needle is hollow with an insulating coating with an electrode mounted on the tip. During the procedure, the EMG needle was used on various muscles in the upper neck that control neck movement. While many neck muscles may be tested for dystonia, only muscles that are overactive via EMG testing are injected with botulinum toxin. In most cases, the overactive muscles are the oblique capitis superior muscle, the oblique capitis inferior, the longissimus capitis, the trapezius, and the levator scapula muscle.

Overactive muscle is believed to provide proprioceptive input to the brain that conflicts with visual and vestibular input. These conflicting inputs lead to vertigo.

The above-described patient experienced consistent resolution of her vertigo symptoms and pain after each treatment for a total of five treatments. During each treatment, all of the neck muscles were tested. Overactive muscles were administered botulinum toxin. The oblique capitis superior and the oblique capitis inferior were consistently injected bilaterally after each treatment.

An important finding for explaining the etiology of cervical vertigo is diagnosis of cervical dystonia, which was confirmed by EMG. It is postulated that cervical muscle overactivity and associated hyperactive muscle spindles provide an altered cervical somatosensory input. The mechanism is proprioceptive, and the sensory mismatch between cervical and vestibular input would be expected to result in cervical vertigo. In the present patient, chemodenervation with botulinum toxin of the dystonic neck muscles reduced muscle spasm and pain, and thus the proprioceptive input resulted in the improvement of her vertigo. Similar changes in proprioceptive input through physiotherapy, acupuncture, and manipulation have been shown to reduce neck pain and dizziness. Likewise, anesthetic muscle blocks to spastic cervical muscles reduce dizziness in patients with cervical spondylosis and in patients with neck pain. Another possible explanation for improving cervical vertigo is decompression of the occipital and sub-occipital nerves and blood vessels by chemodenervation of the overlying muscles. Such decompression would also promote normalization of the afferent input and improve cervical vertigo.

In compliance with the statute, the invention described has been described in language more or less specific as to structural features. It should be understood however, that the invention is not limited to the specific features shown, since the means and construction shown, comprises the preferred embodiments for putting the invention into effect. The invention is therefore claimed in its forms or modifications within the legitimate and valid scope of the amended claims, appropriately interpreted under the doctrine of equivalents.

I claim:

1. A method for treating cervical vertigo in a patient, comprising:

a. selecting an EMG needle with an EMG electrode mounted on a syringe body containing botulinum toxin, said EMG needle connected to an EMG machine configured to identify abnormal EMG activity and selectively inject an amount of said botulinum toxin into said neck muscle;

b. selecting a neck muscle to test using said EMG electrode on said EMG needle from the following group of neck muscles: oblique capitis superior muscle, oblique capitis inferior, the longissimus capitis muscle, the trapezius, and the levator scapula;

c. inserting said EMG electrode on said EMG needle into said selected neck muscle and determining whether said selected neck muscle exhibits abnormal EMG activity; and d. injecting a measured amount of botulinum toxin into said selected neck muscle using said EMG needle if said selected neck muscle is determined to exhibit abnormal EMG activity, e. wherein neck muscles that do not exhibit abnormal EMG activity are not injected with botulinum toxin.

2. The method as recited in claim 1, wherein each subsequent treatment session includes steps a-d.

3. The method as recited in claim 2, wherein each subsequent treatment session is repeated every three months.

4. The method as recited in claim 1, wherein the botulinum toxin is botulinum toxin A.

5. A method for reducing cervical vertigo in a patient, comprising the following steps:

a. selecting an EMG needle configured to conduct a muscle activity test, said EMG needle includes a syringe body containing botulinum toxin A;

b. testing each of the following neck muscles for overactivity using said EMG needle: the oblique capitis superior, the oblique capitis inferior muscle, the longissimus capitis muscle, the trapezius, and the levator scapula; and c. administering 2.5 to 100 units of said botulinum toxin using said EMG needle to each said muscle tested to exhibit.

* * * * *